US00PP21297P3

(12) United States Plant Patent
Kleinhanns

(10) Patent No.: US PP21,297 P3
(45) Date of Patent: Sep. 14, 2010

(54) *SALVIA* PLANT NAMED 'FLORSALDBLUE'

(50) Latin Name: *Salvia nemorosa L.*
Varietal Denomination: Florsaldblue

(75) Inventor: Christoph E. Kleinhanns, Gernrode (DE)

(73) Assignee: Florensis Hamer CS, Hendrik Ido Ambacht (NL)

( * ) Notice: Subject to any disclaimer, the term of this patent is extended or adjusted under 35 U.S.C. 154(b) by 0 days.

(21) Appl. No.: 12/378,037

(22) Filed: Feb. 10, 2009

(65) Prior Publication Data

US 2010/0205705 P1 Aug. 12, 2010

(51) Int. Cl.
*A01H 5/00* (2006.01)

(52) U.S. Cl. ..... Plt./475

(58) Field of Classification Search ..... Plt./475
See application file for complete search history.

*Primary Examiner*—Wendy C. Haas
(74) *Attorney, Agent, or Firm*—Jondle & Associates, P.C.

(57) ABSTRACT

A new *Salvia* plant particularly distinguished by its blue flower color, compact growth habit, long flowershoots and increased resistance to fungal disease is disclosed.

2 Drawing Sheets

Genus and species: *Salvia nemorosa* L.
Variety denomination: 'Florsaldblue'.

BACKGROUND OF THE NEW PLANT

The present invention comprises a new and distinct cultivar of *Salvia*, botanically known as *Salvia nemorosa* L. and hereinafter referred to by the cultivar name 'Florsaldblue'. The new cultivar originated from an uncontrolled cross made in June 2003 in Quedlinburg, Sachsen-Anhalt, Germany. The female parent was a proprietary Salvia plant named '1386' (unpatented). The male parent was an unknown *Salvia* plant.

The new cultivar was first propagated in March 2007 in H.I. Ambacht, The Netherlands, and has been asexually reproduced repeatedly by vegetative cuttings over three generations over approximately a two-year period. The present invention has been found to retain its distinctive characteristics through successive asexual propagations.

Plant Breeder's Rights for this cultivar have not been applied for. 'Florsaldblue' has not been made publicly available more than one year prior to the filing of this application.

SUMMARY OF THE INVENTION

The following are the most outstanding and distinguishing characteristics of this new cultivar when grown under normal horticultural practices in Quedlinburg Sachsen-Anhalt, Germany.

1. Blue flower color;
2. Compact growth habit;
3. Long flowershoots; and
4. High tolerance to fungal diseases.

DESCRIPTION OF PHOTOGRAPHS

This new *Salvia* plant is illustrated by the accompanying photographs which show overall plant habit including blooms, buds, and foliage of the plant; the colors shown are as true as can be reasonably obtained by conventional photographic procedures. The photographs are of a plant about four months old, grown in a greenhouse in Quedlinburg Sachsen-Anhalt, Germany, in the spring of 2008.

DESCRIPTION OF THE NEW CULTIVAR

Figure 1:
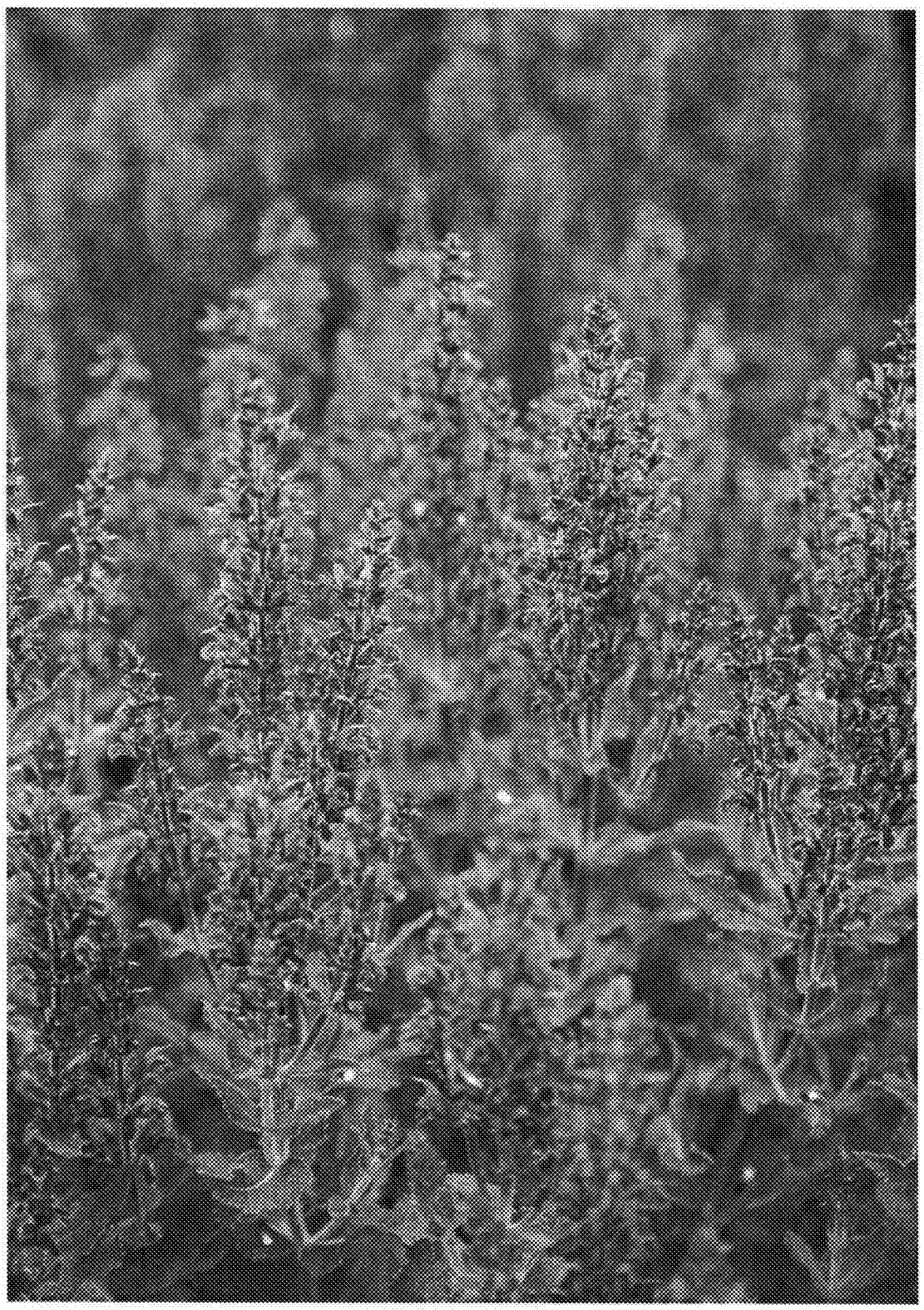
FIG. 1 shows a close-up of the mature flowers.
Figure 2:
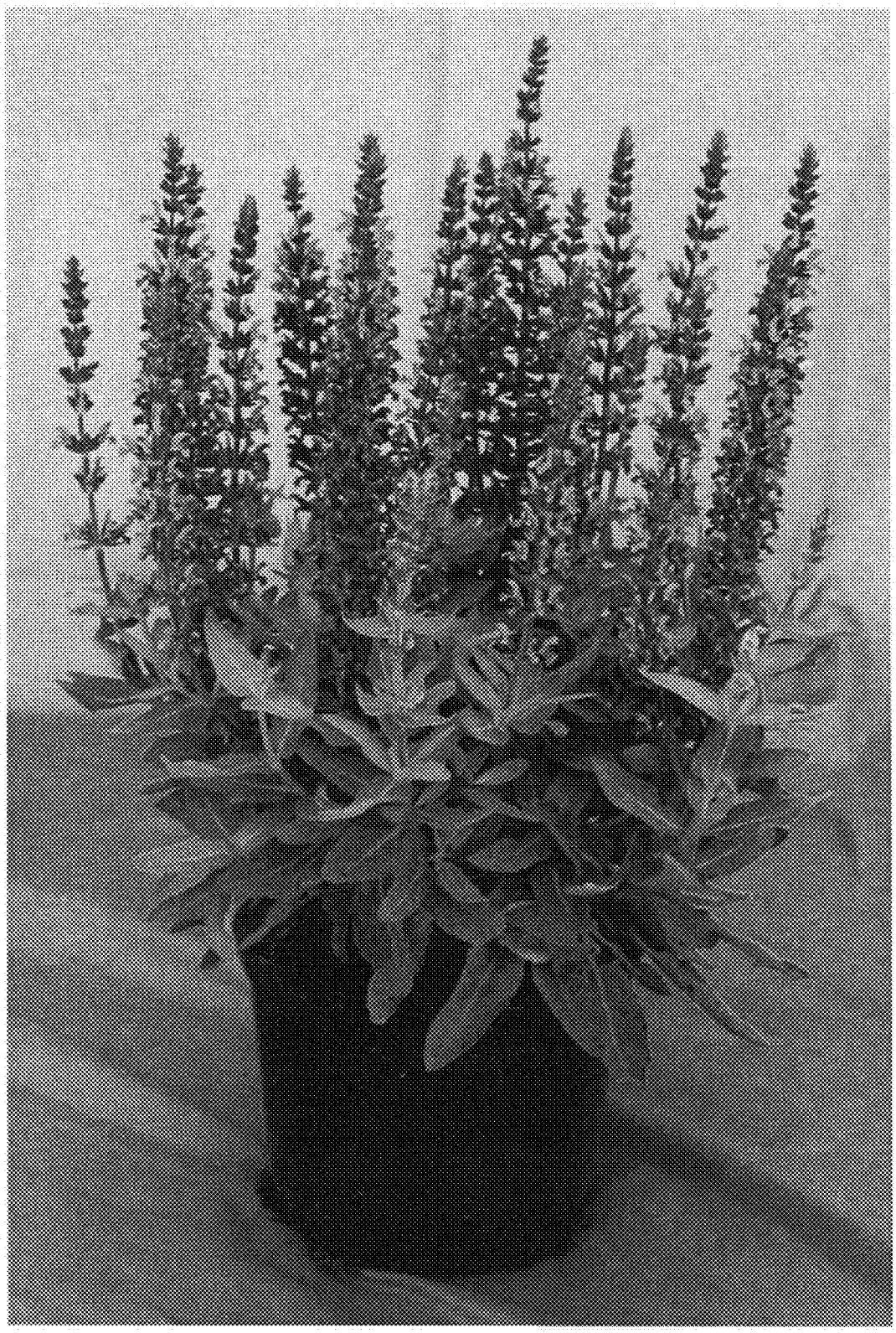
FIG. 2 shows the overall plant habit, including blooms, buds, and foliage.

The following detailed description sets forth the distinctive characteristics of 'Florsaldblue'. The data which defines these characteristics were collected from asexual reproductions carried out in Quedlinburg, Sachsen-Anhalt, Germany. The plant history was taken on four month old plants which were grown in a greenhouse. Color readings were taken under natural light in the greenhouse. The plants were pinched two to three weeks after potting. Color references are primarily to The R.H.S. Colour Chart of The Royal Horticultural Society of London (R.H.S.) (1986).

DETAILED BOTANICAL DESCRIPTION OF THE NEW PLANT

Classification:
- *Botanical name.*—*Salvia nemorosa* L.
- *Common name.*—Woodland Sage.

Parentage:
- *Female parent.*—Proprietary Salvia plant named '1386' (unpatented).
- *Male parent.*—Unknown Salvia plant.

Plant:
- *Form and habit.*—Spreading, upright.
- *Height (from top of soil).*—25.0 cm to 30.0 cm.
- *Width (including flowers).*—30.0 cm.
- *Outdoor plant performance.*—Spring to autumn.

Leaves:
- *Arrangement.*—Opposite.
- *Shape.*—Lanceolate.
- *Apex.*—Acute.
- *Base.*—Subcordate.
- *Margin.*—Crenulate.
- *Immature.*—Length: 2.0 cm to 3.0 cm. Width: 1.5 cm.

*Mature* (*fully expanded*).—Length: 7.0 cm. Width: 2.7 cm to 2.9 cm.
*Color, immature* (*both surfaces*).—RHS 137B (Green) to RHS 137C (Green).
*Color, mature* (*both surfaces*).—RHS 137A (Green) to RHS 137B (Green).
*Venation, immature.*—Type: Reticulate. Color: RHS 145D (Yellow-green).
*Venation, mature.*—Type: Reticulate. Color: RHS 145D (Yellow-green).
*Texture.*—Upper surface: Smooth. Lower surface: Pubescent.
*Petiole.*—Length: 0.2 cm. Diameter: 0.2 cm. Texture: Upper surface: Pubescent. Lower surface: Pubescent.
*Pubescence color* (*both surfaces*).—Lighter than RHS 155A (Transparent).

Stem:
*Length* (*excluding inflorescence*).—20.0 cm to 22.0 cm.
*Diameter.*—0.3 cm to 0.4 cm.
*Internode length.*—2.0 cm to 3.0 cm.
*Texture.*—Pubescent.
*Color.*—RHS 137D (Green).

Flower:
*Arrangement.*—In verticillasters on spikes.
*Shape.*—Spike.
*Flowering season.*—Spring to summer.
*Flower buds.*—Length: 0.4 cm. Diameter: 0.2 cm. Shape: Round. Color: RHS 99A (Blue) to RHS 99B (Blue).
*Inflorescence.*—Length: 12.0 cm. Diameter: 1.5 cm. Quantity of inflorescences per plant: 30 to 50.
*Flowers.*—Diameter: 0.2 cm. Depth/height: 0.8 cm.
*Lastingness of individual blooms on the plant.*—1 to 2 days.
*Fragrance.*—Absent.

Petals:
*Arrangement.*—One upper lip and one lower lip with two lobes; lips fused at the base.
*Length.*—Upper petal: 0.5 cm. Lower petal: 0.3 cm.
*Width* (*both upper and lower petal*).—0.2 cm.
*Shape* (*both upper and lower petal*).—Labiate.
*Apex.*—Upper petal: Obtuse. Lower petal: Rounded.
*Texture* (*both surfaces*).—Slightly pubescent.
*Pubescence.*—Slight.
*Color* (*when opening*).—Upper petal (both surfaces): Blue RHS 93A (Blue). Lower petal (both surfaces): Blue RHS 93B (Blue).
*Color* (*fully open*).—Upper petal (both surfaces): Blue RHS 93A (Blue). Lower petal (both surfaces): Blue RHS 93B (Blue).

Sepals:
*Arrangement.*—2 sepals fused to form a tube.
*Length.*—0.4 cm.
*Width.*—0.25 cm.
*Shape.*—Apiculate.
*Apex.*—Apiculate.
*Base.*—Rounded.
*Margin.*—Smooth.
*Texture* (*both surfaces*).—Smooth.
*Color* (*immature, both surfaces*).—RHS 137C (Green) with RHS 95A (Purple). Color (mature, mature surfaces): RHS 137B (Green) with RHS 95A (Purple). Longitudinal stripes color (immature, both surfaces): RHS 93B (Purple). Longitudinal stripes color (mature, both surfaces): RHS 93A (Purple).

Penduncle:
*Color.*—Lighter than RHS 94D (Transparent lilac).
*Length.*—0.2 cm.
*Diameter.*—0.1 cm.
*Aspect.*—45°.
*Texture.*—Smooth.

Reproductive organs:
*Stamens.*—Quantity per flower: 2. Filament length: 0.1 cm. Filament color: RHS 157D (Transparent white).
*Anther.*—Anther color: Lighter than RHS 85D (Transparent lilac). Length: 0.1 cm.
*Pollen color.*—RHS 161D (Greyed-yellow).
*Pollen amount.*—Moderate.
*Pistil.*—Pistil length: 0.8 cm to 1.0 cm. Pistil quantity: 1.
*Stigma.*—Color: RHS 157D (Transparent white). Shape: Forked.
*Style.*—Length: 0.8 cm to 1.0 cm. Color: RHS 157D (Transparent white).
*Ovary color.*—RHS 141D (Green).

Fruit and seed set: Maximum of 4 oval seeds per flower; often not germinating.

Disease and insect resistance: Resistance is typical of the species, but with a high tolerance for fungal diseases.

COMPARISON WITH PARENTAL AND COMMERCIAL CULTIVARS

'Florsaldblue' differs from the female parent '1386' (unpatented) by having a more compact plant habit with larger flowers than '1386'.

'Florsaldblue' differs from the commercial cultivar 'Markus' (unpatented) by having a compact plant habit with long flowershoots while 'Markus' has a very compact growth habit and short flowershoots.

I claim:

1. A new and distinct cultivar of *Salvia* plant as shown and described herein.

* * * * *